United States Patent [19]
Katdare et al.

[11] Patent Number: 5,622,990
[45] Date of Patent: Apr. 22, 1997

[54] IBUPROFEN LYSINATE PHARMACEUTICAL FORMULATION

[76] Inventors: Ashok Katdare; Chung Y. Lui; Scott N. Kleinbart, all of P.O. Box 4, West Point, Pa. 19403

[21] Appl. No.: 879,086

[22] Filed: May 1, 1992

Related U.S. Application Data

[63] Continuation of Ser. No. 673,613, Mar. 22, 1991, abandoned.

[51] Int. Cl.$^6$ .......................... A01N 31/10; A61K 31/235
[52] U.S. Cl. .......................... 514/533; 514/534; 514/548; 514/570
[58] Field of Search .................................. 514/533, 534, 514/548, 570

[56] References Cited

U.S. PATENT DOCUMENTS

| | | |
|---|---|---|
| 4,279,926 | 7/1981 | Bruzzese et al. . |
| 4,609,675 | 9/1986 | Franz .................................. 514/568 |
| 4,994,604 | 2/1991 | Tung et al. .......................... 562/401 |
| 5,087,454 | 2/1992 | Duerholz et al. . |

FOREIGN PATENT DOCUMENTS 0172014  2/1986  European Pat. Off. .

OTHER PUBLICATIONS

Lieberman and Lachman, *Pharmaceutical Dosage Forms: Tablets*; 1, 61–107 (1980, Marcel Dekker, N.Y.).
Pharmaceutical Dosage Forms: Tablets; 1, 61–107 (1980) Marcel Dekker, N.Y.
The Merck Index, Monographs No. 1961, (11th ed., New Jersey, Merck & Co., Inc., 1989).
Handbook of Pharmaceutical Excipients, (Published by American Association).
The Merck Index, Monographs Nos. 3521 and 5393, (11th ed., N.J., Merck & Co., Inc., 1989).
Physicians Desk Reference, PDR® 43ed., 1384 and 1408, (1989).

Primary Examiner—Rebecca Cook

[57] ABSTRACT

Pharmaceutical ibuprofen lysinate dry granulation formulations comprising about 90% w/w ibuprofen lysinate are useful for the preparation of tablets containing ibuprofen lysinate.

5 Claims, No Drawings

IBUPROFEN LYSINATE PHARMACEUTICAL FORMULATION

This is a continuation of application Ser. No. 07/673,613, filed Mar. 22, 1991, abandoned.

BACKGROUND OF THE INVENTION

Ibuprofen is available in both prescription and OTC dosages for use as an analgesic, anti-inflammatory and antipyretic agent. Certain salts of ibuprofen, such as the basic amino acid salt, particularly the lysine salt may have beneficial properties over the free acid itself. One problem with such salts is that they add to an already high dosage size for ibuprofen. To reduce this problem it is desirable to minimize the inclusion of pharmaceutical excipients with the active agent.

U.S. Pat. No. 4,609,675 ("675") provides a dry granulation pharmaceutical ibuprofen formulation and a process for preparing this formulation. However the "675" formulation requires the use of a disintegrant (croscarmellose sodium) and preferably a flow agent silicon dioxide.

There is no teaching or suggestion in the art for preparing a dry granulation pharmaceutical formulation of ibuprofen lysinate.

DETAILED DESCRIPTION OF THE INVENTION

This invention relates to a pharmaceutical ibuprofen lysinate dry granulation formulation comprising about 90% w/w ibuprofen lysinate.

Included within this invention are formulations containing each of the stereoisomers of ibuprofen lysinate including the racemic mixtures and specifically including the stereoisomer formed from (S)-ibuprofen and (S)-lysine. Furthermore, the hydrates of ibuprofen lysinate, specifically including the monohydrate are included within this invention.

The formulations within the present invention also include one or more excipients selected from agents such as microcrystalline cellulose such as Avicel 102, binding agents such as povidone, and lubricants such as magnesium stearate. In general, a tablet will contain approximately 90% weight/weight ibuprofen lysinate.

The ibuprofen lysinate granulation formulations are prepared by (1) roller compacting the ibuprofen lysinate to manufacture a dry granulation;

(1) mixing the ibuprofen lysinate granulation with at least one excipient;

(3) compressing the mixture to form a tablet.

This invention provides a pharmaceutical dry granulation useful for the production of tablets containing 100 mg to 400 mg ibuprofen lysinate measured in mg ibuprofen. For example, the dry granulation may be adopted for preparing tablets of 200 mg ibuprofen lysine monohydrate. Each tablet is prepared by mixing a dry granulation containing

| | |
|---|---|
| ibuprofen lysine monohydrate | 359.2 mg |
| avicel PH 102 | 18.0 mg |
| povidone | 17.0 mg |
| magnesium stearate | 4.0 mg |

This invention also provides a process for preparing pharmaceutical ibuprofen lysine granulate compositions which are useful in preparing compressed tablet or filled capsules containing from about 100 mg to 400 mg ibuprofen lysinate, measured in weight ibuprofen which comprises:

(1) roller compacting the ibuprofen lysinate to manufacture a dry granulation;

(2) mixing the ibuprofen lysinate granulation with at least one excipient;

(3) compressing the mixture to form a tablet or filling a capsule.

The present invention exhibits the following advantages over current technology for preparing an ibuprofen pharmaceutical composition:

(1) The current formulation does not contain a disintegrant such as that required in U.S. Pat. No. 4,609,675

(2) The current formulation does not contain a "flow-aid" reagent such as silicon dioxide which is stated to be a preferred ingredient in the ibuprofen formulation of U.S Pat. No. 4,609,675

(3) The dry granulation process disclosed herein allows the use of ibuprofen lysinate monohydrate as the active ingredient. Wet granulations requiring a drying step could result in the conversion of the monohydrate to anhydrous drug.

The following examples illustrate the present invention and are not intended to be limiting.

EXAMPLE I

150 mg (S)-ibuprofen-(S)-lysine Caplet

| Table Components | mg/caplet | 500 gm (1674 caplets) |
|---|---|---|
| Dry granulated (S)-ibuprofen-** (S)-lysine monohydrate | 269.4 | 450.97 g |
| Cellulose microcystalline NF avicel PH 102 | 13.5 | 22.59 gm |
| Povidone USP K29/32 (Plasdone) | 12.75 | 21.34 gm |
| Magnesium stearate impallable powder NF | 3.0 | 5.0 gm |

Procedure:
(S)-ibuprofen-(S)-lysine, avicel pH 102 and povidone were mixed in a suitable mixer for 10 minutes. The magnesium stearate was passed through a 60 mesh screen and then added to the mixture and mixed for 5 minutes. The dry granulation was compressed on a suitable tablet press using 7/32" × 17/32" caplet shaped tooling.
** equivalent to 150 mg of dexibuprofen acid

EXAMPLE II

150 mg Dexibuprofen Lysine Caplet

| Table Components | mg/caplet | 500 gm batch size (1748 caplets) |
|---|---|---|
| Dry granulated (S)-ibuprofen-** (S)-lysine monohydrate | 269.4 | 470.91 gm |
| Cellulose microcystalline NF avicel PH 102 | 13.5 | 23.59 gm |
| Magnesium stearate impallable powder NF | 3.0 | 5.24 gm |

Procedure:
(S)-ibuprofen-(S)-lysine and avicel pH 102 were mixed in a suitable mixer for 10 minutes. The magnesium stearate was passed through a 60 mesh screen and introduced into the powder mixture and mixed for 5 minutes. The dry granulation was compressed using a suitable tablet press using 7/32" × 17/32" caplet shaped tooling.
** equivalent to 150 mg of dexibuprofen acid

EXAMPLE III

200 mg Dexibuprofen Lysine Caplet

| Table Components | mg/caplet | 14,304 gm batch size (36,000 caplets) |
|---|---|---|
| Dry granulated (S)-ibuprofen-** (S)-lysine monohydrate | 359.2 | 12,900.0 gm |
| Cellulose microcystalline NF avicel PH 102 | 18.0 | 648.0 gm |
| Magnesium stearate impallable powder NF | 4.0 | 144.0 gm |
| Povidone USP K29/32 (Plasdone) | 17.0 | 612.0 gm |

Procedure:

(S)-ibuprofen-(S)-lysine, avicel pH 102 and povidone were mixed in a suitable mixer for 10 minutes. The magnesium stearate was passed through a 60 mesh screen and added to the dry powder and mixed for 5 minutes. The dry granulation was compressed on a suitable tablet press with 8/32" × 19/32" caplet shaped tooling.

** equivalent to 200 mg of dexibuprofen acid

What is claimed is:

1. A pharmaceutical ibuprofen lysinate dry granulation formulation comprising about 90% w/w ibuprofen lysinate, provided that the formulation does not contain a disintegrant.

2. A composition according to claim 1 wherein the ibuprofen lysinate is present as ibuprofen lysinate monohydrate.

3. An ibuprofen lysinate dry granulation formulation according to claim 1 prepared by
   (1) roller compacting the ibuprofen lysinate to manufacture a dry granulation;
   (2) mixing the ibuprofen lysinate granulation with at least one excipient; and
   (3) compressing the mixture to form a tablet.

4. A formulation according to claim 3 wherein the ibuprofen lysinate is present as (S)-ibuprofen-(S)-lysine monohydrate.

5. A process for preparing a pharmaceutical ibuprofen lysinate dry granulate formulation for preparing compressed tablets or filled capsules containing from 100 to 400 mg of ibuprofen per dosage unit which comprises:
   (1) roller compacting the ibuprofen lysinate to manufacture a dry granulation:
   (2) mixing the ibuprofen lysinate with at least one excipient so that the composition contains about 90% w/w ibuprofen lysinate;
   (3) compressing the mixture to form a tablet or using the mixture to fill a capsule; provided that the formulation does not contain a disintegrant.

* * * * *

UNITED STATES PATENT AND TRADEMARK OFFICE
CERTIFICATE OF CORRECTION

PATENT NO. : 5,622,990

DATED : 4/22/97

INVENTOR(S) : Katdare et al.

It is certified that error appears in the above-identified patent and that said Letters Patent is hereby corrected as shown below:

On the cover page please include

Assignee: Merck & Co., Inc., Rahway, New Jersey

Attorney, Agent or Firm- Richard S. Parr, Catherine D. Fitch, Melvin Winokur

Signed and Sealed this

Eighth Day of July, 1997

*Attest:*

BRUCE LEHMAN

*Attesting Officer*      *Commissioner of Patents and Trademarks*